United States Patent

Crouse et al.

[11] Patent Number: 5,098,400
[45] Date of Patent: Mar. 24, 1992

[54] NEEDLE SHIELD

[75] Inventors: Roger L. Crouse, Ormond Beach, Fla.; Stephen W. Goodsir, Wayne; Paul Y. McCormick, Chester Springs, both of Pa.

[73] Assignee: Sherwood Medical Company, St. Louis, Mo.

[21] Appl. No.: 655,873

[22] Filed: Feb. 14, 1991

[51] Int. Cl.⁵ .............................................. A61M 5/32
[52] U.S. Cl. ..................................... 604/192; 604/263
[58] Field of Search ............... 604/192, 197, 198, 199, 604/263

[56] References Cited

U.S. PATENT DOCUMENTS

| | | | |
|---|---|---|---|
| 2,671,450 | 3/1954 | Dann | 128/218 |
| 2,688,963 | 9/1954 | Smith | 128/216 |
| 2,799,272 | 7/1957 | Peach | 604/263 |
| 2,831,483 | 4/1958 | Delorenzo | 128/218 |
| 2,847,996 | 8/1958 | Cohen et al. | 128/218 |
| 3,865,236 | 2/1975 | Rycroft | 206/364 |
| 4,237,882 | 12/1980 | Wickham | 128/217 N |
| 4,248,246 | 2/1981 | Ikeda | 604/263 |
| 4,317,446 | 3/1982 | Ambrosio et al. | 128/218 R |
| 4,334,536 | 6/1982 | Pfleger | 128/218 DA |
| 4,365,626 | 12/1982 | House | 128/218 DA |
| 4,430,082 | 2/1984 | Schwabacher | 604/263 |
| 4,474,734 | 10/1984 | Cooper | 604/263 |
| 4,485,918 | 12/1984 | Mayer | 206/366 |
| 4,636,201 | 1/1987 | Ambrose et al. | 604/192 |
| 4,728,320 | 3/1988 | Chen | 604/110 |
| 4,735,311 | 4/1988 | Lowe et al. | 604/263 |
| 4,735,617 | 4/1988 | Nelson et al. | 604/192 |
| 4,742,910 | 5/1988 | Staebler | 206/365 |
| 4,752,290 | 6/1988 | Schramm | 604/198 |
| 4,775,367 | 10/1988 | Schmidt | 604/263 |
| 4,826,488 | 5/1989 | Nelson et al. | 604/192 |
| 4,850,970 | 7/1989 | Sutherland | 604/117 |
| 4,872,552 | 10/1989 | Unger | 206/365 |
| 4,897,083 | 1/1990 | Martell | 604/192 |
| 4,900,309 | 2/1990 | Netherton et al. | 604/192 |
| 4,915,697 | 4/1990 | Dupont | 604/192 |
| 4,931,048 | 6/1990 | Lopez | 604/110 |
| 4,964,866 | 10/1990 | Szwarc | 604/192 |
| 4,986,818 | 1/1991 | Imbert et al. | 604/263 |
| 5,002,536 | 3/1991 | Thompson et al. | 604/192 |
| 5,013,299 | 5/1991 | Clark | 604/192 |

Primary Examiner—C. Fred Rosenbaum
Assistant Examiner—Sharon Finkel
Attorney, Agent, or Firm—Andrew J. Beck; Montgomery W. Smith; Gene B. Kartchner

[57] ABSTRACT

The present invention relates to a shield for use on a prefilled hypodermic syringe assembly. The shield is intended to be retrofitable over a sheath/needle sub-assembly of the hypodermic syringe assembly in such a manner that insertion of the sheath/needle sub-assembly into the shield can be simply and easily accomplished by a medical worker, and subsequent extraction of the sheath from the shield is prevented by retention members which are formed from the housing of the shield, and which protrude into the chamber to hold the sheath. The retention member are formed so as to allow the sheath to be easily slidable into the chamber of the shield, yet engage the exterior surface of the sheath to resist extraction thereof once the sheath has engaged the retention members. Also disclosed are unique method of manufacturing the sheath of the present invention along with preferred methods of use thereof.

68 Claims, 3 Drawing Sheets

NEEDLE SHIELD

BACKGROUND OF THE INVENTION

1. Field of the Invention

The present invention relates to a shield for a hypodermic syringe assembly. More particularly, the present invention relates to a shield which can be retrofitted over an existing sheath/needle cannula sub-assembly of a hypodermic syringe assembly. Even more particularly, the present invention relates to a rigid shield which can be retrofitted over a resilient sheath which is being used to seal the distal end of a needle cannula of a prefilled hypodermic syringe prior to its use, the shield functioning to prevent needle sticks due to accidental piercing of the resilient sheath by the needle cannula.

2. Description of the Prior Art

It is common practice in the preparation of medications for use by medical workers, to pre-packaging the medications directly within a sealed hypodermic syringe assembly when such is a necessary vehicle for administration of the medication to a patient. According to this practice, a hypodermic syringe is prefilled with a predetermined amount of medication, and the medication is sealed into the syringe by sealing the distal end of the needle cannula. The syringe is then packaged singly or in a predetermined quantity, into packaging which can be sterilized and maintain the sterility of the syringes until the medication is to be administered to a patient. In following this procedure, it has often been the practice to seal the distal end of the needle cannula with a resilient needle sheath. A sheath of this type is usually formed of a resilient rubber material with an elongate cavity therein which can accept the needle cannula. Generally, the sheath is formed so as to be capable of forming a friction fit with the hub of the needle cannula to hold the sheath in position over the needle. The cavity is sized so as to either fit snugly around the distal tip of the needle cannula, or allow the distal tip of the needle cannula to pierce the distal end of the sheath and become embedded therein. In either case, the sheath effectively seals the tip of the needle cannula to prevent fluid from flowing therethrough out of the syringe during storage or prior to use.

Although the resilient needle sheath as generally quite successful in sealing the needle cannula, there remains serious concerns in the use thereof, specifically, due to the piercability of the sheath, there exists a possibility of medical workers accidentally receiving a needle stick while using the syringe. This usually occurs either during preparation of the syringe for administration of medication to a patient, or during disposal procedures therefor. For example, since the sheath is formed of a resilient rubber, a minimal force improperly applied is all that is needed to cause the needle tip to penetrate (and even pierce entirely through) the sheath. Therefore, inadvertent pressure on the tip of the sheath while the needle is properly placed therein, may cause the needle to pierce entirely through the sheath's distal end and become exposed.

Further, medical workers often attempt to reinsert the needle into the sheath after the syringe has been used and prior to its disposal, even though this procedure is generally not recommended. Misalignment of the needle with the sheath during reinsertion can cause the tip of the needle to pierce through the side of the sheath where it may contact the hand of the medical worker holding it. Needle protrusion of this nature can readily occur since the tip of commonly used needles is ground off-center (i.e. on a bias) and therefore does not proceed in a linear path when piercing the resilient sheath material. Instead, the needle tends to follow the off centered point as it passes through the sheath and in effect "skives off" in an arcing path of travel as it passes through the sheath material. If a medical worker is not extremely careful to let the needle center itself in the sheath cavity during reinsertion, the needle may inadvertently contact the side of the sheath cavity and pierce through the sheath material in a surprisingly unexpected direction, catching the medical worker off guard and likely causing a stick to the hand of the medical worker which is being used to hold the sheath.

Although rigid, substantially impenetrable shields are commonly used to cover needle cannulas of hypodermic syringe assemblies, they are generally unsuitable for use on syringes which have been prefilled with a fluid such as a liquid medicament due to their inability to seal the end of the needle cannula from fluid flow therethrough during storage and prior to use.

There have been attempts in the past to develop a substantially impenetrable shield which can be positioned over a resilient sheath commonly used on prefilled syringes in order to provide added protection to a medical worker from accidental needle sticks. For example, U.S. Pat. No. 4,964,866 to Szwarc discloses a needle shield assembly for use on a prefilled syringe. The assembly includes a resilient sheath, generally of the above described prior art construction, permanently enclosed in a rigid shield. The entire needle shield assembly (including the resilient sheath permanently enclosed in the rigid shield) is positioned over the needle cannula and thus seals the lumen of the needle cannula while simultaneously preventing needle sticks due to an accidental protrusion of the needle through the sheath.

Although this invention is a substantial improvement over the use of a resilient sheath alone in preventing accidental needle sticks, it is nevertheless somewhat limited in its use, and generally unadaptable to the myriad of different structural designs of commonly used prefilled hypodermic syringe assemblies. Specifically, the Szwarc needle shield assembly cannot be conveniently used to retrofit previously filled, sheathed, and sterilized prefilled hypodermic syringe assemblies. Also, the design of the Szwarc device prevents its use as a retrofittable sub-assembly over a previously sheathed hypodermic syringe in order to afford the added protection of the substantially impenetrable shield against the possibility of needle sticks. Contrarily, the Szwarc shield is manufactured in such a way as to require its assembly about the sheath prior to the sheath's placement over the needle cannula, thus preventing any use thereof as a retrofit over a previously sheathed and sterilized needle cannula.

There exists therefore a need to develop a shield which can be retrofitted over a sheath of a prefilled hypodermic syringe assembly by a medical worker after the sheath has been positioned, and prior to using the assembly. Further, it is necessary that such retrofitting procedure not compromise the sterility of the needle prior to its use.

An attempt to use the Szwarc device in a retrofit manner would necessitate the removal of the original resilient sheath which was placed over the needle cannula prior to its sterilization, and subsequent insertion thereover of Szwarc's sheath/needle sub-assembly. Such a procedure would likely not be recommended due to the possibility of contamination of the needle cannula during the retrofitting process.

There also exists a need in the prior art to develop a needle shield which can be used on various sizes and lengths of needle cannula and sheaths therefor. Since it is important for a sheath to be properly sized in order to seal a needle cannula, the Szwarc device, in order to properly function to seal a needle cannula, must generally be manufactured to dimensions required by a particular syringe assembly design. Therefore, other needle cannula's (and sheath's therefor) of a substantially different size (e.g. shorter or longer in length) than specifically anticipated by Scwarc's design, cannot be used therewith.

Staebler, in U.S. Pat. No. 4,742,910, teaches a needle sheath holder which consists of a hollow barrel member adapted to be held in the hand of a medical worker, which includes a protective plate mounted to an open end of the barrel through which a sheath/needle sub-assembly of a hypodermic syringe assembly can be inserted. The plate is designed to protect the medical worker's hand during the insertion process. The Staebler device also includes a plurality of flexible gripper members attached at the barrel opening, which are intended to engage the needle sheath so as to retain the needle sheath within the barrel.

Although the Staebler device seems an improvement over the Szwarc device in its retrofit capabilities, it nevertheless suffers from several drawbacks. Most notably, the Staebler device includes three separate parts (i.e., the barrel, the plate, the gripper members) which must be individually manufactured and subsequently assembled, resulting in relatively expensive manufacturing costs. Further, it is not readily evident from the Staebler disclosure that a sheath formed of resilient material, such as resilient rubber (as opposed to what seems to be shown by Staebler as a relatively rigid sheath) could be successfully inserted into and retained by Staebler's barrel shield. There therefore exists a need in the prior to develop a retrofittable shield for use over a resilient sheath of a hypodermic syringe assembly which is simple in design and inexpensive to manufacture.

In U.S. Pat. No. 4,636,201 to Ambrose et al. teaches the placement of a rigid shield over a rubber sheath of a hypodermic syringe. The rigid shield includes a plurality of spaced teeth members which are located at (and essentially form) the opening of the shield through which the sheath/needle sub-assembly of the syringe assembly is to be inserted. At least a pair of the teeth of the shield include a lip which projects inwardly toward the center of the opening for closing in over the proximal end of the sheath once completely inserted into the shield.

Although Ambrose et al. allows a retrofit procedure to be performed on a hypodermic syringe assembly in a manner similar to Staebler, and also anticipates use of its device over a resilient sheath, there are nevertheless several important drawbacks of the Ambrose et al. device. Specifically, due to the Ambrose et al. design, there remains a chance for accidental needle sticks to a medical worker even after the tip of the needle has already been inserted into the shield. This is due to the necessary placement of the open slots between adjacent teeth at the open end of the shield. In other words, there exists the possibility of a needle entering the shield at such an angle that it may subsequently pass back out of the shield through one of the slots and result in a stick the medical worker.

More importantly, due to the location of the teeth on the Ambrose et al. device, it is difficult to ensure that a proper grip of the teeth about the proximal end of the sheath will occur. Many prior art sheath designs call for insertion of the sheath over the syringe needle hub until the proximal end of the sheath abuts a shoulder of the hub (generally at a location where the hub changes from a larger to a smaller diameter). This is a common design characteristic of syringe and is useful to insure sealing of the sheath over the needle hub. It also gives medical workers a visual and tactile indication that the sheath is properly positioned on the hub. In such designs, there is no room for the teeth of the Ambrose et al. device to slip between the hub shoulder and the proximal end of a properly placed sheath in order to grip and retain the sheath in the manner disclosed. Due to this fact, use of the Ambrose et al. device on many common needle hub and sheath design will not allow the teeth of the shield to properly attach themselves about the proximal end of the sheath. Only syringes having a sheath/needle design which does not include abutment of the proximal end of the sheath against a shoulder of the needle hub will function properly with the Ambrose et al. device. Such a design limitation substantially inhibits the use of the Ambrose et al. device for purposes of retrofitting various common prefilled hypodermic syringe assemblies.

Further, medical workers may be hesitant to employ the Ambrose et al. device for retrofitting over sheaths of hypodermic syringe assemblies if they feel the shield may be less than completely reliable in gripping and retaining the sheath (e.g., due to the difficulties it may encounter if used on syringe assemblies having a design of the sheath/needle sub-assembly connection which differs from that shown in the Ambrose et al. disclosure).

Although it may seem at first glance that this problem may be avoided by initially partially removing the sheath from the needle hub prior to inserting the sheath into the Ambrose et al, shield (in order to space the proximal end of the sheath from the hub shoulder) such a procedure would likely be very unpopular with the medical workers due to the inconvenience thereof. Such would also likely fail to resolve the problem since the teeth of the Ambrose et al. needle shield, contact and are forced apart by the sheath as the shield is positioned thereover. The teeth therefore force the sheath in the direction of the needle hub during placement of the shield. Subsequently, any attempt to separate the proximal end of the sheath from a shoulder of the needle hub prior to placement of the shield would be opposed by the force of the teeth on the sheath and likely replace the proximal end thereof into abutting relationship with the shoulder of the needle hub prior to complete insertion of the sheath into the shield. The result would again be that the teeth would not be able to properly and securely grip the sheath.

There therefore exists a need in the prior art to develop a shield which can retrofitted over an existing sheath of a prefilled hypodermic needle assembly and retain the sheath in the shield during subsequent removal and/or insertion of the needle into the sheath, without regard to the particular design of the sheath-/needle hub connection.

Although the above prior art discloses a plurality of rigid shields used to protect medical workers against needle sticks from hypodermic syringes having resilient sheaths, there nevertheless continues to be a need for a rigid, substantially impermeable needle shield which can be simply and easily retrofitted over a range of sizes and designs of prefilled hypodermic syringes, without compromising the sterility of the needle cannula and with complete reliability of retention of the sheath in the shield. Further, such a needle shield is needle which can also be manufactured as a single integral unit requiring no assembly of individual parts, so as to be simple to manufacture and relatively inexpensive.

OBJECTS AND SUMMARY OF THE INVENTION

It is an object of the present invention to provide a shield for use on a prefilled hypodermic syringe having a resilient sheath thereover, which is easily retrofittable over the sheath and which permanently retains the sheath therein once the shield is retrofitted thereover.

It is another object of the present invention to provide a retrofittable shield, such as described above, which can be used on a variety of sizes of sheath/needle cannula sub-assemblies of prefilled hypodermic syringe assemblies.

It is further an object of the present invention to provide a shield as described above which is easily manufacturable as a single integral unit in an efficient and inexpensive manner.

These and other objects of the present invention are disclosed, by way of example and not necessarily by way of limitation, in presently preferred embodiments thereof. A needle shield made in accordance with the principles of the present invention includes an elongate tubular housing having formed therein an elongate chamber, preferably open at its proximal end. The housing includes retention members preferably formed therefrom, which protrude into the chamber and which may be oriented in a predetermined pattern and shaped so as to allow insertion of a resilient sheath (which covers a needle cannula) into the chamber with minimal resistance, yet allow sufficient gripping to inhibit removal of the sheath from the chamber after insertion. The present invention is intended to function to cause the sheath to remain inside the shield once inserted therein, throughout all subsequent normal uses of the hypodermic syringe assembly.

If desired, the retention members may be oriented in a plurality of specific longitudinal positions within the chamber of the shield, to allow the shield to be used in conjunction with a plurality of different sizes (e.g. various lengths) of sheath/needle cannula sub-assemblies of hypodermic syringe assemblies. Each retention member, or set of retention members, may be located in the chamber of the shield so as to allow a particular shield to be usable on a variety of sheath/needle cannula lengths.

In one preferred method of manufacture of a needle shield in accordance with the principles of the present invention, the housing of the shield may be formed along with the elongate channel therein in a single operation step, such as by injection molding or the like. Subsequently, in a second operational step, a piercing tool is pushed through the housing into the chamber in at least one location. The piercing tool operates to shear a portion of the housing away from the remainder thereof as it is pushed through, and causes the sheared portion to protrude into the chamber. The piercing tool may be sized and shaped so as to generate a sheared portion of the housing which is of a predetermined size and shape so as to be usable without further modification, as a retention member to retain the sheath.

If desired, the piercing tool may be oriented along the housing of the shield prior to its piercing thereof, in such a manner that the retention member formed by the piercing tool will be properly located and oriented within the chamber so that a sheath inserted into the chamber can easily slide past the retention member while moving in the direction of insertion and become engaged and entrapped by the retention member so as to inhibit or prevent any attempt at extraction of the sheath.

In a preferred method of use of the present invention, a syringe assembly, such as a prepackaged, sterile, prefilled syringe assembly which includes a sheath/needle cannula sub-assembly, can be removed from its sterile packaging (if necessary) by a medical worker, and a shield formed in accordance with the principles of the present invention, taken from its own prepackaged sterile container (if necessary), can be slid over the sheath/needle sub-assembly. Due to the various possible locations of retention members within the chamber of the shield, the sheath/needle cannula sub-assembly need be of no specific length to be properly accommodated within the chamber of the shield and adequately retained therein against extraction. When it is desired to use the hypodermic syringe assembly, the medical worker need merely remove the shield from the syringe assembly, which simultaneously, due to the interengagement of the shield and the sheath, removes the shield from the needle cannula.

After use of the syringe assembly, the shield, along with the sheath therein, can be repositioned over the needle cannula if desired without the fear of needle sticks occurring due to accidental piercing of the sheath by the needle cannula during reinsertion thereof.

The needle shield of the present invention may optionally be formed with the chamber having an open or closed distal end, and/or may optionally include stopper elements in the chamber at the distal end thereof for preventing over insertion of the sheath.

These and other objects and advantages of the present invention will become apparent from the following more detailed description when taken in conjunction with the accompanying drawings in which like elements are identified with like numerals throughout.

DETAILED DESCRIPTION OF THE PREFERRED EMBODIMENTS

In the exemplary drawings, used for the purposes of illustration, an embodiment of a needle shield made in accordance with the principles of the present invention is referred to generally by the reference numeral 10. The shield 10 is provided for use with the prefilled hypodermic syringe assembly 11 in order to prevent needle sticks to a medical worker from needle cannula 12.

Figures 1, 2, 3:
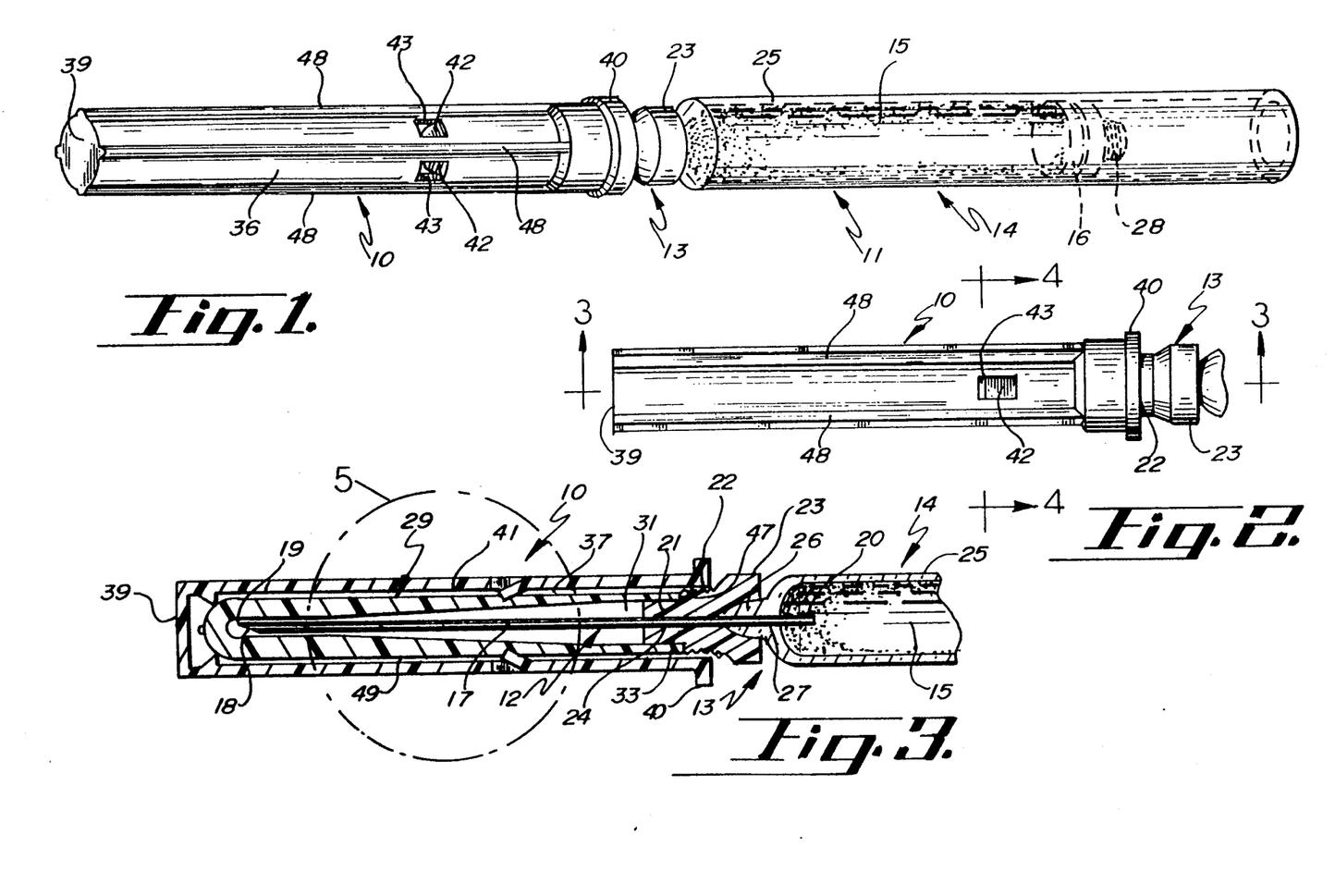
FIG. 1 is a perspective view of a preferred embodiment of a needle shield formed in accordance with the principles of the present invention, affixed to a prefilled hypodermic syringe assembly.
FIG. 2 is a side elevation view of the needle shield of FIG. 1 made in accordance with the principles of the present invention, affixed over the sheath/needle cannula sub-assembly portion of the prefilled hypodermic syringe assembly.
FIG. 3 is a longitudinal cross-sectional view of the needle shield and sheath/needle cannula sub-assembly of FIG. 2 taken along line III—III of FIG. 2.

As best shown in FIGS. 1-3, the prefilled hypodermic syringe assembly 11 generally includes a needle cannula 12 affixed by hub 13 to a syringe barrel 14. The barrel 14, commonly made of transparent glass, contains a fluid medicament 15 which is trapped therein by piston 16.

The needle cannula 12 is formed with a lumen 17 extending through the entire length thereof, and includes a distal opening 18 adjacent its beveled distal tip 19. A proximal opening 20 of the needle cannula 12 is in fluid communication with the lumen 17 and the interior of the barrel 14.

The needle cannula 12 is affixed to the barrel 14 by hub 13. The hub 13 forms a distal cylindrical surface 21, an intermediate cylindrical surface 22, and a proximal cylindrical surface 23, each of which function to allow a friction fit of the hub 13 with other elements of the syringe assembly 11 in a manner as will be further explained below. The hub 13 also includes cavity 24 through which the needle cannula 12 passes, and an abutment should 47.

The barrel 14 of the syringe assembly 11 is preferably formed of a transparent glass sidewall 25 of cylindrical shape which includes a closed tip 26 at the distal end thereof. The tip 26 is affixed in fluid tight permanent connection to cavity 24 of the hub 13. Tip 26 also includes a channel 27 through which the needle cannula 12 passes. The needle cannula 12 is permanently affixed to the channel 27 in any well known fluid-tight manner. During use of the hypodermic assembly 11, the fluid medicament 15 is forced through opening 20 of the lumen 17 of the needle cannula 12, by forcing piston 16 in a distal direction in barrel 14. Prior to movement of piston 16, a piston arm (not shown) can be readily attached to threaded extension 28 thereof for convenience in operating the piston 16.

Figure 6:
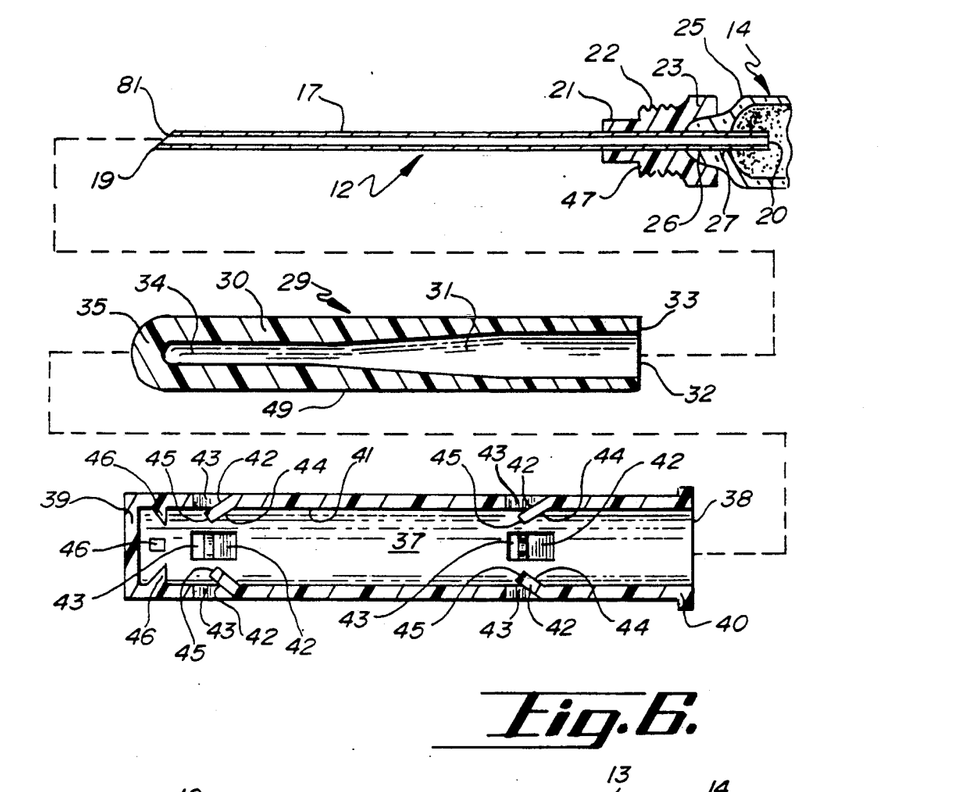
FIG. 6 is an expanded cross-sectional view of a second preferred embodiment of the needle shield of the invention, and the sheath/needle cannula sub-assembly of FIG. 3.

As best shown in FIGS. 3 and 6, the sheath 29 is formed of a elongate cylindrical plug 30 of resilient material, such as rubber, and includes a cavity 31 sized to accept the needle cannula 12 therein. The proximal portion 32 of cavity 31 is sized to allow its retention over cylindrical surface 21 of the hub 13 in a friction fit connection. The proximal end surface 33 of the sheath 29 which surrounds opening 32 is intended to be placed in abutting relationship with the shoulder 47 of the hub 13 when the sheath 29 is properly positioned thereon.

The distal portion 34 of cavity 31 is formed of a reduced diameter which is equal to, or only slightly greater, than the outer diameter of needle cannula 12. When the needle cannula 12 is properly inserted in the sheath 29, the distal end 35 of the sheath 29 (which forms distal portion 34 of the cavity 31), effectively seals the distal opening 18 of the lumen 17 and substantially retains the fluid medicament 15 within the confined area of the barrel 14 and the lumen 17.

An alternative embodiment (not shown) of the sheath 29 may include forming the cavity 31 such that no distal portion 34 thereof exists. In other words, instead of cavity 31 extending from proximal opening 32 in a distal direction in a gradually reducing diameter through distal portion 34 at the distal end 35 thereof, the cavity 31 stops well short of the distal end 35 leaving the remainder of the distal end 35 of the sheath 29 uniformly formed of resilient material. A needle cannula 12 inserted into this alternative type sheath 29 pass through the cavity 31 and pierces into the distal end 35 of sheath 29 until the lumen opening 18 thereof is completely embedded in the resilient material forming distal end 35 (and until the opening 32 and proximal end surface 33 become properly positioned on the hub 13 in the manner as explained above). Since the lumen opening 18 of the needle cannula 12 is completely embedded within the resilient material forming the sheath 29, the fluid medicament 15 is therefore completely sealed with barrel 14 and lumen 17.

As far as the needle shield of the present invention is concerned, either design of sheath 29, including sheaths having other types of inner cavities 31 designed for sealing the distal opening 18 of a needle cannula 12, are hereby noted as being compatible for use with the needle shield 10 of the present invention. The needle sheath 29 as shown herein is intended to be only exemplary of the types of needle sheaths which can be accommodated by the needle shield 10 of the present invention.

As referred to in this disclosure, the above-described hypodermic syringe assembly 11 is intended to be understood as describing the needle cannula 12, hub 13, barrel 14 and sheath 29. Further as referred to herein, the sheath/needle cannula sub-assembly is intended to identify the portion of assembly 11 which includes sheath 29 and needle cannula 12.

As best shown in FIG. 3, the needle shield 10 of the present invention may include a generally elongate cylindrically-shaped housing 36 formed of a relatively rigid material so as to be generally impermeable to penetration by the needle cannula 12. Any common well-known metal or polymeric material exhibiting these characteristics may be used, the preferred embodiment of the present invention being formed of polypropylene.

The housing 36 of the shield 10 has formed therein an elongate generally cylindrical chamber 37. The chamber 37 is formed with at least a proximal end opening 38 through which the sheath/needle cannula sub-assembly can be inserted.

If desired, although not required by the present invention, a distal end closure 39 may be formed to close the distal end of the chamber 37. If present, the distal end closure 39 can function to prevent over insertion of a sheath 29 within chamber 37, by functioning as a stop against which distal end 35 of the sheath 29 must ultimately abut when completely inserted into chamber 37. Alternatively, the distal end of chamber 37 may be left open, i.e., formed without distal end closure 39, and stopping members 46 may be formed therein to function as stops for preventing the distal end 35 of sheath 29 from passing therebeyond during insertion. It should be well noted that stops 46 and/or distal end closure 39, are both optional structural features of the shield 10 of the present invention and may be used together, singly, or not at all, as desired.

The open end 38 of chamber 37 may include a flange 40 extending around the entire circumference thereof to protect the medical worker's hand during operation of the shield 10. The flange 40 may be of any radial dimension desired depending on the particular intended use of the shield 10, and the degree of user safety required. For example, should it be a routine necessity after a particular use of the present invention that the shield 10 be re-inserted over a used needle cannula 12, the flange 40 may be formed of a generally large radial diameter in order to increase protection to the worker's hand in case of inadvertent misalignment of the needle cannula 12 with proximal end opening 38 of the shield 10 during re-insertion. If however, the shield 10 is intended to be used only for protection during storage and prior to use of the syringe assembly 11, the flange 40 may be of the smaller radial diameter (as shown in the drawings) or may be omitted entirely from the shield 10, as desired.

As best shown in FIG. 3, the interior surface 41 of chamber 37 is generally cylindrical in shape and sized to a diameter which is intended to be slightly larger than the diameter of the exterior surface 49 of the sheath 29. At at least one location on interior surface 41, a retention member 42 protrudes therefrom into the chamber 37. Further, the retention member 42 is designed so as to contact the exterior surface 49 of the sheath 29 when the sheath is inserted into the chamber 37. The retention member 42 is designed to allow it to slide over sheath surface 49 as long as the sheath 29 is moving in the direction of insertion into chamber 37. However, once sheath 29 has been inserted beyond the retention member 42, attempted extraction of the sheath 29 causes the retention member 42 to increase its frictional force against surface 49 in an amount proportional to the force being used in extracting the sheath 29 from the chamber 37. In other words, force used to attempt an extraction of the sheath 29 from chamber 37 is opposed by the retention member 42. Increases in the retraction force are subsequently opposed by an increase in the gripping force of the retention member 42 against the sheath surface 49. Thus, removal of the sheath 29 once inserted into the shield 10 beyond the retention member 42 is inhibited or substantially prevented.

Figure 7:
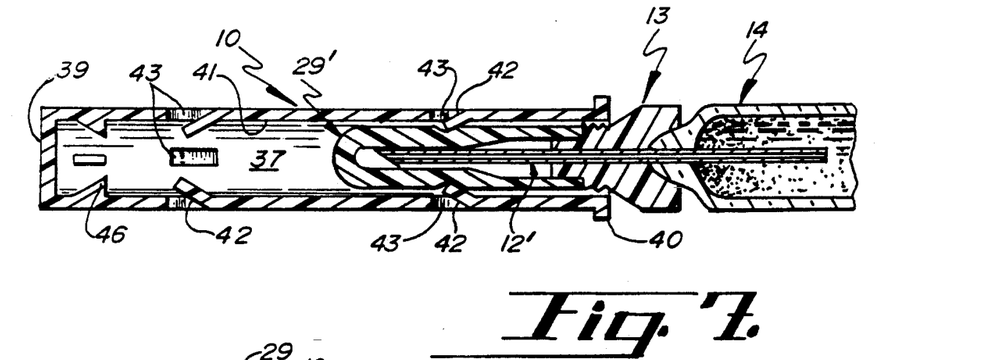
FIG. 7 is a cross-sectional view of the second preferred embodiment of the needle shield formed in accordance with the principles of the present invention, being used with an alternative type sheath/needle cannula sub-assembly.

In the particular embodiment of the shield 10 as shown in FIGS. 1-5 and in the second preferred embodiment as shown in FIGS. 6 and 7, the retention member 42 is formed directly from the sidewall 36 of the shield 10 by piercing the sidewall 36 with a tool (not shown) designed to shear a section of the sidewall 36 away from the remainder thereof, and bend the sheared section (42) into the chamber 37. The tool pierces an opening 43 in the sidewall 36 and forms the retention member 42 within the chamber 37.

Figure 4:
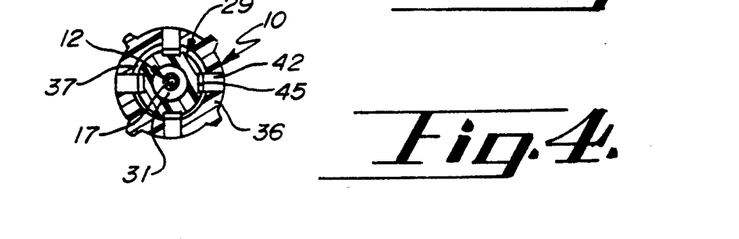
FIG. 4 is a perpendicular cross-sectional view of the needle shield and sheath/needle cannula sub-assembly of FIG. 2 taken along line IV—IV of FIG. 2.
Figure 5:
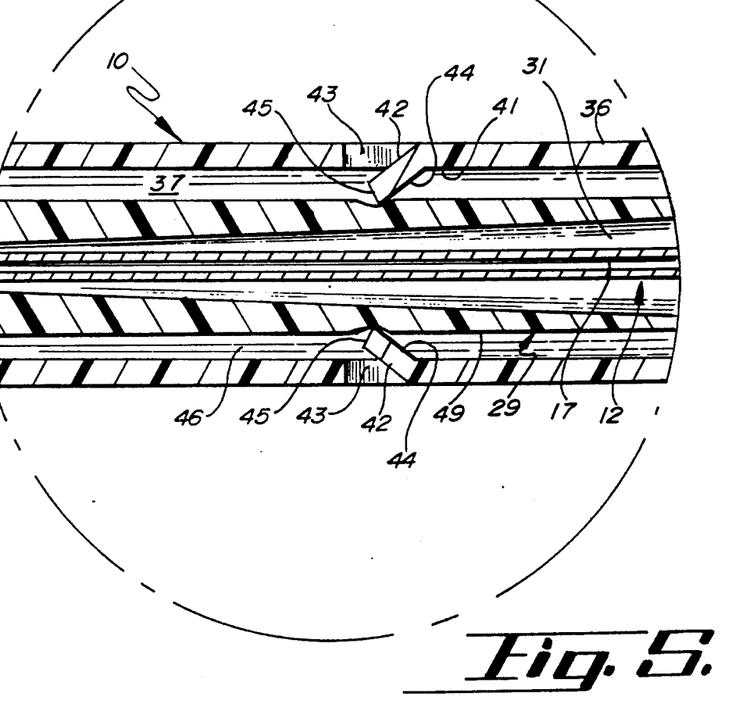
FIG. 5 is an enlarged view of the middle portion of the shield of the present invention shown in the area of V of FIG. 3.

The retention member 42 comprises a surface 44 (which previously was part of interior surface 41) and a sheared end surface 45 (which previously was part of sidewall 36). As best shown in FIGS. 3 through 5, the retention member 42 takes the form of a barb and includes the surface 44 which will make initial contact with the surface 49 of sheath 29 as it is inserted into the chamber 37. Insertion of sheath 29 into chamber 37 causes sheath surface 49 to force retention member 42 at least back (at least partially) into opening 43 and allows the sheath to slide therepast. However, when sheath 29 is subjected to extraction forces, a slight movement of the surface 49 thereof will cause the sheared end surface 45 of the retention member 42 to be drawn in toward the sheath 29, thus increasing the resistance of the retention member 42 against the movement of the sheath 29 to inhibit and subsequently prevent extraction of the sheath 29.

The retention member 42 may be used alone or in conjunction with other retention members. For example, similarly formed and uniformly spaced retention members 42 may be located at positions around the chamber surface 41 to increase the gripping performance thereof during use. For example, as best shown in FIG. 4, a particular useful orientation of a plurality of retention members 42 would be to locate a plurality of retention members 42 in uniformly spaced apart locations around a single circumferential position in the chamber 37. Such a grouping of retention members 42 (identified hereinafter as a "set" of retention members) could be placed in chamber 37 at a location predetermined to be useful in retaining a particular length or lengths of sheath 29. Further if desired, as shown in the second preferred embodiment of the present invention in FIGS. 6 and 7, a plurality of sets of retention members 42 may be positioned along the longitudinal axis of the shield 10 in order to adapt the shield 10 for use with more than one size of sheath/needle cannula sub-assembly.

Particularly, as shown in FIG. 7, a relatively short needle cannula 12' covered by a relatively short sheath 29' may be engaged by a set of retention members 42 which are located toward the proximal end opening 38 of the shield 10. The shield 10 may be manufactured with a secondary set of retention members 42 located closer to the distal end of the shield 10, in order to allow the single shield 10 to be used on any of a number of lengths of sheath/needle cannula subassemblies. In either of the first or second preferred embodiment of the present invention it is clear that a "generic" shield 10 can be manufactured and subsequently used to retrofit a plurality of various sizes or lengths of sheath/needle cannula sub-assemblies of various prefilled hypodermic syringe assembly designs (which of course may be similar to or very different from the syringe assembly 11 shown in the drawings).

The shield 10 of the present invention as shown in FIGS. 1 through 7 can be manufactured in a plurality of ways. One of the preferred methods of manufacturing the present invention is to form the housing 36 with chamber 37 therein in a single manufacturing process such as injection molding. As stated above, the housing 36 will include an open proximal end 38 formed as a part of channel 37, (opening 38 having generally the same diameter as the interior surface 41). The housing 36 may optionally include flange 40, closed end 39, stop elements 46 and reinforcement ribs 48, all formed integrally therewith as desired.

In a second manufacturing process, the shield 10 is then pierced in any one of a number of predetermined locations to form openings 43 in the housing 36 and to cause retention member 42 to protrude into chamber 37.

The piercing process and the tool used therefor, can be chosen to form the appropriate size and protrusion of retention members 42 for proper functioning of the shield during insertion and retention of the sheath 29 therein. For example, a shield 10 having a cylindrical chamber 37 with an interior diameter of approximately 0.20 inches, may be formed with a retention member 42 therein which effective reduce the diameter through which the sheath 29 must pass to approximately 0.15 inches. A sheath 29 having an outer diameter of approximately 0.19 inches would therefore be required to contact surface 44 of the retention member 42 to force it to move somewhat toward the interior surface 41 of the chamber 37 to allow the sheath 29 to move therepast into a completely inserted position within chamber 37. Once the sheath 29 is inserted, the sheared end surfaces 45 of the retention members 42 is locked in intimate contact with surface 49 of the sheath 29, and any subsequent extraction force of the sheath 29 would be immediately opposed by surfaces 45 to prevent any substantial retractional movement of the sheath 29.

The shield 10 of the present invention is very simple and reliable in use. For example, a medical worker can merely insert the sheath/needle cannula sub-assembly of a hypodermic syringe assembly 11 into the shield 10 at any time prior to its use. If desired, the hypodermic syringe assembly 11 may be manufactured as a unit and packaged singly or in quantities, separated apart from the shield 10. The shield 10 may be similarly packaged separately from the syringe 11, either singly or in quantities. A medical worker would then perform the retrofit procedure him or herself by removing an assembly 11 from its sterile package and a shield 10 from its package and retrofitting the shield 10 thereto by inserting the sheath/needle cannula sub-assembly completely into the chamber 37 of the shield 10. In this manner, the sterility of the needle cannula 12 is unaffected by the retrofit procedure, and the assembly 11 is made substantially safe from inadvertent needle sticks which may have resulted from bumping or applying excessive pressure to the distal end 35 of the sheath 29 prior to the positioning of the shield 10 thereover.

When it is desired to use the syringe assembly 11 to deliver the medication 15 therein to a patient, the medical worker can remove shield 10 from the assembly 11. Removal of shield 10 simultaneously causes the removal of sheath 29 therewith, thus exposing the needle for use. A piston arm (not shown) can be attached to threaded end 28 of the piston 16 if desired, and the medical worker can then administer the medication 15 to the patient.

After use, should it be necessary for the medical worker to reinsert the needle cannula 12 into the sheath 29, the medical worker is substantially protected from a needle stick due to the type of misalignment of the needle cannula 12 in the sheath 29 which would cause tip 19 thereof to prematurely penetrate the plug material 30 and "skive" off from its intended path and protrude through the exterior surface 49. Should such occur, instead of the medical worker receiving a stick from the tip 19 of the needle cannula 12, the tip 19 becomes embedded in the substantially impermeable housing 36 of the shield 10 and is prevented from reaching the medical workers hand which is holding the shield 10.

Figure 8:
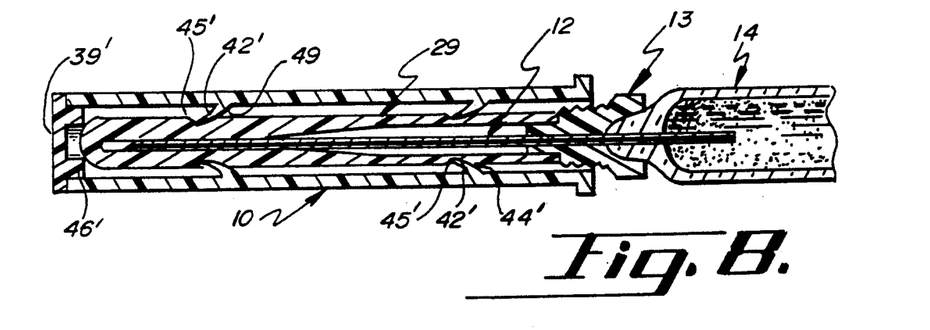
FIG. 8 is a longitudinal cross-sectional view of a third preferred embodiment of a needle shield formed in accordance with principles of the present invention.

As best shown in FIG. 8, an alternative embodiment of the present invention is shown as shield 10' Shield 10' is substantially similar to shield 10 of the first preferred embodiment herein except that the retention members 42' have been formed as a part of the molding process of the housing 36' instead of in a secondary manufacturing step.

It will be apparent from the forgoing, while particular embodiments have been illustrated and described, various modifications can be made thereto without departing from the spirit and scope of the invention. Accordingly, it is not intended that the invention be limited, except as by the appended claims.

What is claimed:

1. A shield for a hypodermic syringe assembly which includes a sheath/needle sub-assembly having a resilient sheath covering a distal portion of a needle cannula, said shield comprising:

a relatively rigid housing forming an elongate chamber therein, said chamber forming an open proximal end, and said chamber and said open proximal end having cross-sectional areas sized to allow the sheath/needle sub-assembly to be inserted through said open proximal end and into said chamber; and retention means formed as a part of said housing and permanently located within said chamber away from said open proximal end, for locking the sheath within said chamber to prevent separation of the sheath from said shield when the needle cannula is removed from the sheath, said retention means including at least one retention member having a sliding surface and a barbed end;

whereby said shield is easily positionable over the sheath/needle sub-assembly, and said sliding surface contacts the sheath during insertion thereof, and the sheath, when engaged within said shield, is easily removable from the needle cannula by removing said sheath, and said barbed end functions to grip and retain the sheath against subsequent retraction of the sheath from said chamber.

2. A shield according to claim 1 wherein said retention means forms an effective cross-sectional area of said chamber which is less than the cross-sectional area of the sheath.

3. A shield according to claim 2 wherein said retention means includes at least one retention member projecting into said chamber and functioning to allow movement of the sheath/needle sub-assembly into said chamber and subsequently to automatically inhibit movement of the sheath out of said chamber.

4. A shield according to claim 3 wherein said at least one retention member is relatively resilient when subjected to forces thereagainst caused by the sheath/needle sub-assembly as it is inserted into said shield, and relatively rigid when subjected to forces thereagainst caused by the sheath during attempted retraction thereof from said shield.

5. A shield according to claim 1 wherein said at least one retention member is located directly adjacent to and partially forms an opening extending through said housing into said chamber.

6. A shield according to claim 5 wherein said housing is formed of a generally cylindrical outer surface and said chamber is formed of a generally cylindrical inner surface.

7. A shield according to claim 6 wherein said housing includes a plurality of reinforcement ribs integrally formed with an extending longitudinally along said cylindrical outer surface of said housing.

8. A shield according to claim 7 wherein said opening formed at least partially by said at least one retention member is located between at least two of said plurality of reinforcement ribs.

9. A shield according to claim 3 including a plurality of said retention members, said plurality of retention members forming at least one set of retention members spaced uniformly about a circumference of said chamber.

10. A shield according to claim 9 including at least two of said sets of retention members, each of said sets being located at a different longitudinal position along said chamber, whereby said shield is adapted to receive and retain sheath/needle sub-assemblies of varying lengths.

11. A shield according to claim 2 wherein said cross-sectional area of said chamber is a circular area and said effective cross-sectional area is an effective circular area formed by said retention means.

12. A shield according to claim 11 wherein said circular area is approximately 0.20 inches in diameter and said effective circular area is approximately 0.15 inches in diameter.

13. A shield according to claim 1 wherein said elongate chamber further includes a closed distal end.

14. A shield according to claim 13 further including stop means located adjacent said distal end of said chamber, for abutment against a distal end of the sheath to prevent insertion of the sheath beyond said stop means.

15. A shield according to claim 14 wherein said closed distal end of said chamber comprises a enclosure means affixed to said housing, said stop means being integrally formed with said plug means.

16. A shield according to claim 1 wherein said housing is formed of a generally cylindrical outer surface and said chamber is formed of a generally cylindrical inner surface.

17. A shield according to claim 16 wherein said cylindrical outer surface includes a plurality of reinforcement ribs integrally formed with and extending longitudinally along said cylindrical outer surface of said housing.

18. A shield according to claim 1 further including flange means integrally formed with and extending radially outward from said housing at a location adjacent said open proximal end of said chamber.

19. A shield according to claim 1 made from polypropylene.

20. A shield according to claim 1 wherein said chamber includes an open distal end.

21. A shield according to claim 20 further including stop means located in said chamber adjacent said opened distal end, for abutment with a distal end of the sheath for preventing insertion of the sheath beyond said stop means.

22. A shield according to claim 21 wherein said stop means is integrally formed with said housing and extends into said chamber at a location adjacent said open distal end.

23. A method of using a shield for a hypodermic syringe assembly which includes a sheath/needle sub-assembly having a resilient sheath covering the distal portion of a needle cannula, said sheath including a relatively rigid housing forming an elongate chamber therein, the chamber having an open proximal end and a retention means including at least one retention member permanently located within said chamber and away from the chamber open end and formed as a part of the housing, for locking the sheath within the chamber to prevent separation of the sheath from the chamber when the needle cannula is removed, said at least one retention member including a sliding surface and a barbed end, said method of using the shield comprising the steps of:
inserting the sheath/needle sub-assembly through the open proximal end of the chamber until the sheath engages and slides along the sliding surface of the at least one retention member;
removing the sheath from the needle cannula by removing the shield while the retention means holds the sheath in locked position therein, the barbed end of the at least one retention member gripping and retaining the sheath against subsequent retraction of the sheath from the chamber.

24. A method according to claim 23 further including the step of:
replacing the sheath with the shield affixed thereabout, over the needle cannula.

25. A method according to claim 24 further including the step of:
removing the hypodermic syringe assembly from a sterile package prior to inserting the sheath/needle sub-assembly thereof into the shield.

26. A method according to claim 23 wherein the shield includes a plurality of retention members forming at least two sets of retention members, each set of retention members including a plurality of retention members space uniformly about a circumference of the chamber and each set of retention members is located at a different longitudinal position along the chamber, said step of inserting the sheath/needle sub-assembly into the chamber further includes engaging at least one of the sets of retention member with the sheath.

27. A method according to claim 26 wherein said step of engaging the sheath with the retention members includes engaging said sheath with only one set of retention members.

28. A method according to claim 26 wherein said step of engaging the sheath with the retention members includes engaging the sheath with at least two sets of retention members.

29. A method according to claim 23 wherein the chamber is cylindrical in shape having a circular cross-sectional area through which the sheath must pass during insertion, and the retention means forms an effective cross-sectional area which is less than the cross-sectional area of the chamber and less than the cross-sectional area of the sheath, said step of inserting the sheath/needle sub-assembly into the chamber further includes the step of resiliently deforming the sheath as it passes beyond the retention means during insertion thereof into the chamber.

30. A method according to claim 23 wherein the shield further includes stop means located adjacent the distal end of the chamber and said method further includes the step of abutting a distal end of the sheath against the stop means at the completion of said inserting step, the stop means functioning to prevent further insertion of the sheath into the chamber beyond the stop means.

31. A method of making a shield for a hypodermic syringe assembly which includes a sheath/needle sub-assembly having a resilient sheath covering a distal portion of a needle cannula, said method of making the shield comprising the steps of:
forming a relatively rigid housing with an elongate chamber therein, with the chamber being formed with an open proximal end, the open proximal end of the chamber being formed to a size sufficient to allow the sheath/needle sub-assembly to be insertable therethrough into the chamber; and forming a retention means within the chamber away from the open proximal end for locking the sheath within the chamber when the shield is positioned thereover, said step of forming a retention means includes forming at least one retention member having a sliding surface and a barbed end, said sliding surface of said at least one retention member contacting the sheath during insertion thereof and being relatively resilient when subjected to forces thereagainst caused by the sheath/needle sub-assembly as it is inserted into the shield, and said barbed end of said at least one retention member being relatively rigid when subjected to forces thereagainst caused by the sheath during attempted retraction thereof from the shield, the barbed end functioning to grip and retain the sheath within the chamber.

32. A method according to claim 31 wherein the step of forming a retention means includes forming at least one retention member which projects into the chamber.

33. A method according to claim 32 wherein said step of forming at least one retention member includes forming a plurality of retention members which comprise a set of retention members which are spaced uniformly about a circumference of the chamber.

34. A method according to claim 33 wherein said step of forming at least one set of retention members further includes forming two sets of retention members, each set being located at a different longitudinal position along the chamber.

35. A method according to claim 31 wherein said step of forming a relatively rigid housing with an elongate chamber therein includes forming the chamber into a generally cylindrical shape.

36. A method according to claim 35 wherein said step of forming the chamber into a cylindrical shape includes forming the chamber to a diameter of approximately 0.20 inches, and said step of forming a retention means in the chamber includes forming the retention means within the chamber which have an effective cross-sectional diameter of approximately 0.15 inches.

37. A method according to claim 31 wherein said step of forming a relatively rigid housing includes forming a closed distal end in the elongated chamber formed by the housing.

38. A method according to claim 31 wherein said step of forming a relatively rigid housing with an elongate chamber therein further includes forming stop means within the elongated chamber whereby a stop means can contact a distal end of a sheath when inserted into the chamber and prevent insertion of the sheath beyond the stop means.

39. A method according to claim 37 wherein said step of forming a relatively rigid housing with an elongate chamber includes forming a enclosure means to close a distal end of a chamber, and further includes forming stop means integrally with the enclosure means, for contact of a distal end of a sheath to prevent insertion of the sheath beyond the stop means.

40. A method according to claim 31 further including the stop of forming flange means integrally with, and extending radially outward from, the housing at a location adjacent the open proximal end of the chamber.

41. A method according to claim 31 wherein the shield is formed from polypropylene.

42. A method according to claim 31 wherein said step of forming an elongate chamber within the relatively rigid housing includes forming the chamber with an open distal end.

43. A method according to claim 42 including the further steps of a plug means sized to cover the open distal end of the chamber, said step of forming the plug means including forming stop means integrally covering the open distal end of the chamber with the plug means such that the stop means are located within the chamber.

44. A method according to claim 31 wherein said step of forming a retention means includes forming at least one retention member by piercing through the housing of the shield into the chamber thereof to force a portion of the housing into the chamber to form the retention member.

45. A method according to claim 44 wherein said step of forming a relatively rigid housing includes forming the housing of a generally cylindrical outer surface and forming the chamber of a generally cylindrical inner surface, and forming a plurality of reinforcement ribs integrally with, and extending longitudinally along, the cylindrical outer surface of the housing.

46. A method according to claim 44 wherein said step of piercing the housing to form a retention member includes piercing the housing in a plurality of locations to form a plurality of retention members.

47. A method according to claim 46 wherein the step of forming a plurality of retention members includes forming at least one set of retention members circumferentially about the chamber wall in uniform spaced apart relationship.

48. A method according to claim 47 wherein said step of forming a plurality of retention members includes forming the retention members in between the reinforcement ribs.

49. A shield for insertion over and retention of a sheath of a hypodermic syringe assembly which has been formed by the process of:

forming a relatively rigid housing having an elongate chamber therein, the chamber being formed with an open proximal end which is sized to allow a sheath/needle sub-assembly of the hypodermic syringe assembly to be insertable therethrough into the chamber; and forming a retention means within the chamber away from the open proximal end for retaining and locking the sheath within the chamber when the shield is positioned thereover, said step of forming at least one retention including forming a sliding surface and a barbed end on the at least one retention member whereby the sliding surface can contact the sheath during insertion thereof and the barbed end can grip and retain the sheath against subsequent attempts to retract the sheath from the chamber.

50. A shield according to claim 49 wherein the step of forming a retention means includes forming at least one retention member which projects into the chamber.

51. A shield according to claim 46 wherein said step of forming at least one retention member includes forming a plurality of retention members which comprise a set of retention members which are spaced uniformly about a circumference of the chamber.

52. A shield according to claim 51 wherein said step of forming at least one set of retention members further includes forming two sets of retention members, each set being located at a different longitudinal position along the chamber.

53. A shield according to claim 49 wherein said step of forming a relatively rigid housing with an elongate chamber therein includes forming the chamber into a generally cylindrical shape.

54. A shield according to claim 53 wherein said step of forming the chamber into a cylindrical shape includes forming the chamber to a diameter of approximately 0.20 inches, and said step of forming a retention means in the chamber includes forming the retention means within the chamber which have an effective cross-sectional diameter of approximately 0.15 inches.

55. A shield according to claim 49 wherein said step of forming a retention means includes forming at least one retention member which is relatively resilient when subject to forces thereagainst caused by the sheath/needle subassembly as it is inserted into the shield and relatively rigid when subjected to forces thereagainst caused by the sheath during attempted retraction thereof from the shield.

56. A shield according to claim 49 wherein said step of forming a relatively rigid housing includes forming a closed distal end in the elongated chamber formed by the housing.

57. A shield according to claim 49 wherein said step of forming a relatively rigid housing with an elongate chamber therein further includes forming stop means within the elongated chamber whereby a stop means can contact a distal end of a sheath when inserted into the chamber and prevent insertion of the sheath beyond the stop means.

58. A shield according to claim 56 wherein said step of forming a relatively rigid housing with an elongate chamber includes forming a enclosure means to close a distal end of a chamber, and further includes forming stop means integrally with the enclosure means, for contact of a distal end of a sheath to prevent insertion of the sheath beyond the stop means.

59. A shield according to claim 49 further including the stop of forming flange means integrally with, and extending radially outward from, the housing at a location adjacent the open proximal end of the chamber.

60. A shield according to claim 49 wherein the shield is formed from polypropylene.

61. A shield according to claim 49 wherein said step of forming an elongate chamber within the relatively rigid housing includes forming the chamber with an open distal end.

62. A shield according to claim 61 including the further steps of a plug means sized to cover the open distal end of the chamber, said step of forming the plug means including forming stop means integrally covering the open distal end of the chamber with the plug means such that the stop means are located within the chamber.

63. A shield according to claim 49 wherein said step of forming a retention means includes forming at least one retention member by piercing through the housing of the shield into the chamber thereof to force a portion of the housing into the chamber to form the retention member.

64. A shield according to claim 63 wherein said step of forming a relatively rigid housing includes forming the housing of a generally cylindrical outer surface and forming the chamber of a generally cylindrical inner surface, and forming a plurality of reinforcement ribs integrally with, and extending longitudinally along, the cylindrical outer surface of the housing.

65. A shield according to claim 63 wherein said step of piercing the housing to form a retention member includes piercing the housing in a plurality of locations to form a plurality of retention members.

66. A shield according to claim 65 wherein the step of forming a plurality of retention members includes forming at least one set of retention members circumferentially about the chamber wall in uniform spaced apart relationship.

67. A shield according to claim 66 wherein said step of forming a plurality of retention members includes forming the retention members in between the reinforcement ribs.

68. A method of using a shield for a hypodermic syringe assembly which includes a sheath/needle subassembly having a resilient sheath covering the distal portion of a needle cannula, said sheath including a relatively rigid housing forming an elongate chamber therein, the chamber being cylindrical in shape having a circular cross-sectional area through which the sheath must pass during insertion and including an open proximal end, and a retention means including a plurality of tension member located from the chamber open end and formed as part of the housing, the retention members including a sliding surface and a barbed end and being relatively resilient when subjected to forces there against caused by the sheath/needle sub-assembly as it is inserted into the shield and relatively rigid when subjected to forces there against caused by the sheath during attempted retraction thereof from the shield, the retention means forming an effective cross-sectional area which is less the cross-sectional area of the chamber and less than the cross-sectional area of the sheath, said method of using the shield comprising the steps of:
 inserting the sheath/needle sub-assembly through the open proximal end of the chamber,
 contacting the sheath and the sliding surface of the retention members during insertion of the sheath into the chamber and resiliently deforming the sheath as it passes beyond the retention means during insertion thereof into the chamber,
 removing the sheath from the needle cannula by removing the shield while the barbed end of the retention members contacts and grips the sheath to retain the sheath against subsequent retraction thereof from the chamber.

* * * * *

UNITED STATES PATENT AND TRADEMARK OFFICE
CERTIFICATE OF CORRECTION

PATENT NO. : 5,098,400

DATED : March 24, 1992

INVENTOR(S) : Roger L. Crouse, et al

It is certified that error appears in the above-identified patent and that said Letters Patent is hereby corrected as shown below:

On title page, item [73] the assignee should read --American Home Products Corporation, New York, N.Y.--.

Signed and Sealed this

Twentieth Day of April, 1993

Attest:

MICHAEL K. KIRK

*Attesting Officer*     *Acting Commissioner of Patents and Trademarks*